United States Patent [19]

Marquez et al.

[11] 4,446,315

[45] May 1, 1984

[54] ADENOSINE 5'-TRIPHOSPHATE-4-CARBOXAMIDE-RIBOFURANOSYLTHIAZOLE

[75] Inventors: Victor E. Marquez, Gaithersburg; David A. Cooney, Bethesda; Gulilat Gebeyehu, Silver Spring; Hiremagalur N. Jayaram, Gaithersburg, all of Md.

[73] Assignee: The United States of America as represented by the Department of Health and Human Services, Washington, D.C.

[21] Appl. No.: 423,241

[22] Filed: Sep. 24, 1982

[51] Int. Cl.[3] ............................................. C07H 19/20
[52] U.S. Cl. ..................................... 536/27; 424/180; 536/29
[58] Field of Search ....................... 536/27, 23, 24, 28, 536/29

[56] References Cited

U.S. PATENT DOCUMENTS

| | | | |
|---|---|---|---|
| Re. 29,835 | 11/1978 | Witkowski et al. | 536/23 |
| 3,493,558 | 2/1970 | Samejima et al. | 536/27 |
| 3,534,017 | 10/1970 | Fujimoto et al. | 536/27 |
| 3,798,209 | 3/1974 | Witkowski et al. | 536/23 |
| 3,804,826 | 4/1974 | Scheit et al. | 536/27 |
| 3,897,415 | 7/1975 | Robins et al. | 536/23 |
| 3,927,216 | 12/1975 | Witkowski et al. | 536/23 |
| 3,976,545 | 8/1976 | Witkowski et al. | 536/23 |
| 4,138,547 | 2/1979 | Christensen et al. | 536/23 |
| 4,211,771 | 8/1980 | Witkowski et al. | 536/23 |

OTHER PUBLICATIONS

Kovacs et al., "J. Med. Chem.", vol. 25, No. 2, 1982, pp. 107–108.

Cooney et al., "Biochemical Pharmacology", vol. 31, No. 11, pp. 2133–2136.

*Primary Examiner*—Johnnie R. Brown
*Attorney, Agent, or Firm*—John S. Roberts, Jr.

[57] ABSTRACT

The present invention relates to the preparation of and the antitumor compound, adenosine 5'-(trihydrogen diphosphate) 5'→5'-ester with 4-carboxamide-2-$\beta$-D-ribofuranosylthiazole.

1 Claim, No Drawings

ADENOSINE 5'-TRIPHOSPHATE-4-CARBOXAMIDE-RIBOFURANOSYLTHIAZOLE

The present invention relates to the preparation of the antitumor compound, adenosine 5'-(trihydrogen diphosphate) 5'→5'-ester with 4-carboxamide-2-β-D-ribofuranosylthiazole (TAD).

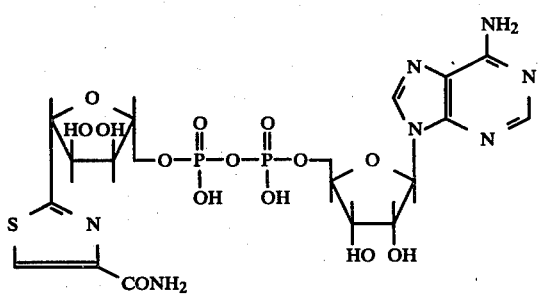

STATEMENT OF PRIOR ART

Cooney et al, "The Conversion of 2-β-D-ribofuranosylthiazole-4-carboxamide to an Analogue of NAD with Potent IMP-dehydrogenase-inhibitory Properties," *Biochemical Pharmacology*, Vol. 31 No. 11, pp. 2133–36, 1982.

Robins et al, "2-β-D-Ribofuranosylthiazole-4-carboxamide, a Novel Potential Antitumor Agent for Lung Tumors and Metastases," *Journal of Medicinal Chemistry*, 25:107 (1982).

Kultan et al, "Possible Mechanisms of Action of 2-β-D-ribofuranosylthiazole-4-carboxamide in Chinese Hamster Ovary Cells," *Proc. Amer. Assoc. for Cancer Res.*, Article #859, Apr. 28–May 1, 1982.

U.S. Pat. No. 3,798,209 Witkowski et al
U.S. Pat. No. 3,897,415 Robins et al
U.S. Pat. No. 3,927,216 Witkowski et al
U.S. Pat. No. 3,976,545 Witkowski et al
U.S. Pat. No. 4,138,547 Christensen et al
U.S. Pat. No. 4,211,771 Witkowski et al
U.S. No. RE 29,835 Witkowski et al The Robins et al article above demonstrates the antitumor efficacy of 2-β-D-ribofuranosylthiazole-4-carboxamide. This drug is metabolized to a NAD (nicotinamide adenine dinucleotide)-like material (TAD) which is responsible for the antitumor effect via inhibition of inosine monophosphate (IMP)dehydrogenase. Initial experiments indicate that the metabolite is active when administered as such. This finding is important since resistant strains do not form TAD when the parent drug is administered.

Utility Statement

The present compound substitutes a ring 4-carboxamide thiazole for the ring fraction 3-carboxamide pyridyl in NAD (nicotinamide adenine dinucleotide); confer *Principles of Medicinal Chemistry*, 2d ed., Lee and Febiger eds., Foye, p. 547, 1981. In action the present compound TAD, which is structurally similar to NAD, substitutes for that compound where NAD acts as a co-enzyme functioning as the hydride ion carrier in systems such as in the inhibition of inosine-5'-monophosphate (IMP) dehydrogenase. The role of IMP (inosine monophosphate) and its control in early steps of purine synthesis is described in Foye above, pages 718–720.

The object of this invention is the preparation of an antitumor compound identified as the active metabolite of the known drug 2-β-D-ribofuranosylthiazole-4-carboxamide (TR). This active metabolite (TAD) is a new chemical compound with antitumor activity superior to that of its progenitor.

THE INVENTION

The chemical synthesis of thiazole-4-carboxamide-adenine dinucleotide (TAD), previously identified as the active anabolite of the oncolytic 2-β-D-ribofuranosylthiazole-4-carboxamide (TR), has been achieved using three different approaches: (1) incubation of AMP and TR-5'-monophosphate (TRMP) with excess DCC (dicyclohexyl carbodiimide) in aqueous pyridine; (2) reaction of adenosine-5'-phosphoromorpholidate with TRMP in pyridine; and (3) reaction of adenosine-5'-phosphoric di-n-butylphosphinothioic anhydride with TRMP in the presence of $AgNO_3$. While the first approach was not successful commercially to produce TAD, the last two afforded 11% and 16% yields, respectively, of isolated TAD. The synthetic TAD was indistinguishable from the biologically produced material as judged by its HPLC behavior, NMR, UV and MS spectra, enzymatic resistance to alkaline phosphatase and susceptibility by venom phosphodiesterase, IMP dehydrogenase inhibitory activity, and cytotoxicity.

It has previously been reported by Cooney et al, *Biochem. Pharmacol.*, 31:2133, 1982, that the oncolytic C-nucleoside, 2-β-D-ribofuranosylthiazole-4-carboxamide (TR, 1a) was anabolized to an analog of NAD which was responsible for the potent inhibition of IMP-dehydrogenase (IMPD) and subsequent depression of all guanine nucleotides. Presence of a phosphodiester linkage in the structure of the anabolite was first surmised from its enzymatic resistance to alkaline phosphatase and susceptibility to venom phosphodiesterases. Subsequently, the structure was completely elucidated by $^1$H-NMR and mass spectral studies. The results were consistent with a NAD analog structure (3a) in which the nicotinamide portion had been supplanted by thiazole-4-carboxamide. This anabolite, TAD, became an interesting target for chemical synthesis. An initial biochemical synthesis from ATP and the 5'-monophosphate of TR (1b, TRMP) in the presence of NAD pyrophosphorylase was satisfactory only as a laboratory preparation.

The present invention presents three different approaches to the synthesis of TAD. Initially, TRMP (1b) or its diammonium salt and AMP (2a) were reacted in the presence of excess dicyclohexylcarbodiamide (DCC) in aqueous pyridine at standard temperature and pressure.

This procedure was similar to one originally used for the synthesis of NAD (Hughes, et al, *J. Chem. Soc.*, 1957, p. 3733). However, this method afforded only a small amount of TAD which was characterized by its HPLC retention time and IMPD inhibitory activity. An improvement over the first method was achieved by selectively activating one nucleotide before the coupling reaction. Therefore, AMP (2a) was converted to its phosphoromorpholidate derivative (2b) and reacted with TRMP (1b) (as the tri-n-octylamine salt) in a monoaryl solvent such as a pyridine or substituted pyridine for 1–3 hrs. at 50°–70° C. A preferred process is for 2 hrs. at 60° C. Among the substituted pyridines are preferred the picolines. This procedure afforded pure isolated TAD (3a) in 9% yield. A modified version of this reaction, which consisted in stirring the two reagents in pyridine or a methyl substituted pyridine such as a picoline or lutidine for 4-8 days at room temperature and up to 60° C., increased the yields of TAD to only 12% [Example 6, Method (a)]. Finally, another activated form of AMP, adenosine-5'phosphoric di-n-butylphosphinothioic anhydride (2c), consistently produced a 16% yield of TAD when reacted with TRMP in the presence of a soluble silver salt such as $AgNO_3$ [Example 6, Method (b)].

TAD was purified by two successive ion exchange chromatographies to afford the final product as the monoammonium salt. The only other contaminant present was ammonium formate which came from the eluent employed in the chromatography. Complete elimination of this salt was achieved by repeated lyophilizations. The most salient features of the spectral data corresponding to TAD are listed in the table below, Table 1.

Biological Activity

A rigorously desalted preparation of TAD was examined for its ability to inhibit a partially purified preparation of IMP dehydrogenase from P388 leukemic cells. On kinetic analysis, with NAD as the variable substrate, formally non-competitive inhibition was observed with a $K_i \sim 0.12$ μM (Table 2). This value was in good agreement with the $K_i$'s of the dinucleotide isolated ex vivo and with that synthesized enzymatically. Against bacterial IMP dehydrogenase chemically synthesized TAD exhibited a $K_i$ of 3.4 μM. Both chemically as well as biologically synthesized TAD proved to be cytotoxic to P388 cells in culture with a median inhibitory concentration of 3.5 and 2.5 μM, respectively (Table 2). These values are not significantly different.

TABLE 2
Biological Activity of TAD

| Source | IMP Dehydrogenase Inhibitory Activity $K_i$ (μM) | Type of Inhibition | Cytotoxicity Against P388 Leukemic Cells in Culture $IC_{50}$ (μM) |
|---|---|---|---|
| of TAD | | | |
| Enzymatic | 0.23 | NC | 2.5 |
| Chemical | 0.12 | NC | 3.5 |

Legend:
Procedures for the synthesis of TAD by enzymatic and chemical means are described in the examples. Analysis of IMP dehydrogenase inhibitory activity and cytotoxicity of these preparations are detailed in the examples. NC stands for non-competitive inhibition.

TABLE 1
SPECTRAL CHARACTERISTICS OF TAD AND ITAD $^1$H-NMR$^a$

| Compound | Sugar Adenosine H1' | Sugar TR H1' | Base Adenosine H2 | Base Adenosine H8 | Base TR H5 | Protective Group 2',3'-Isopropylidene* CH | Protective Group 2',3'-Isopropylidene* CH | P—NMR$^b$ | MS$^c$ MH | UV max |
|---|---|---|---|---|---|---|---|---|---|---|
| TAD | 6.06 (d,J = 6) | 5.04 (d,J ' 4) | 7.96 (s) | 8.17 (s) | 8.40 (s) | | | −11.17 | 670 | 252 |
| ITAD* | 5.95 (d,J = 5.6) | 5.07 (d,J = 2.6) | 7.75 (s) | 7.95 (s) | 8.18 (s) | 1.76 (s) | 1.56 (s) | | 710 | |

$^a$Chemical shifts are given in ppm (δ) relative to TSP.
$^b$Chemical shifts are given in ppm (δ) relative to 80% $H_3PO_4$. The sample contained ethylenediaminetetraacetic acid (EDTA).
$^c$Positive ion mode FAB mass spectrum.
*ITAD = isopropylidene TAD In view of its pyrophosphate linkage, TAD was expected to show a typical AB quartet in the $^{31}$P-NMR spectrum that is characteristic of NAD. However, the two phosphate groups appeared to be magnetically equivalent and only one signal was observed. This was also the case with the reduced form of NAD and it is probable that in this respect TAD resembles more NADH than NAD.

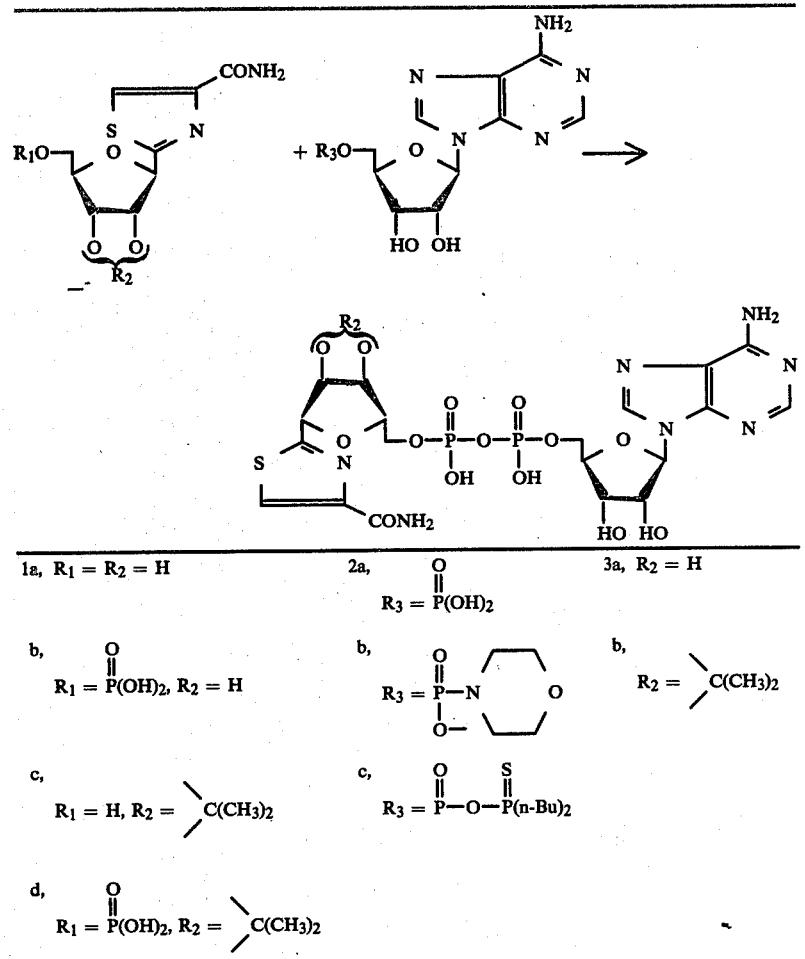

1a, $R_1 = R_2 = H$    2a, $R_3 = \overset{O}{\underset{\|}{P(OH)_2}}$    3a, $R_2 = H$ b, $R_1 = \overset{O}{\underset{\|}{P(OH)_2}}, R_2 = H$    b, $R_3 = \overset{O}{\underset{\underset{O-}{|}}{\underset{\|}{P}}}-N\diagup\!\!\diagdown O$    b, $R_2 = \diagdown\!\!\!\!\diagup C(CH_3)_2$ c, $R_1 = H, R_2 = \diagdown\!\!\!\!\diagup C(CH_3)_2$    c, $R_3 = \overset{O}{\underset{\|}{P}}-O-\overset{S}{\underset{\|}{P}}(n\text{-}Bu)_2$ d, $R_1 = \overset{O}{\underset{\|}{P(OH)_2}}, R_2 = \diagdown\!\!\!\!\diagup C(CH_3)_2$

EXAMPLES

HPLC analyses were performed on a Waters Associates chromatograph equipped with a Partisil 10-SAX column using a gradient-system of 0.01 M to 0.5 M $(H_4N)H_2PO_4$ in 30 min. $^1$H-NMR sectra were recorded in a Varian XL-200 spectrometer. Positive and negative ion mass spectra were obtained on VG Micromass 7070E mass spectrometer equipped with VG fast atom bombardment (FAB) ion sources operated at an accelerating voltage of 4 KV. Elemental analyses were performed by Galbraith Laboratories, Inc., Knoxville, TN.

EXAMPLE 1

Diammonium salt of 2-β-D-ribofuranosyl-thiazole-4-carboxamide 5'-phosphate (1b)

Phosphoryl chloride (0.36 mL, 4 mmol) was added to triethyl phosphate (6 mL) and cooled to 0° C. Water (0.036 mL) was then added and the mixture stirred for 5 min. Immediately after, 1a (1.04 g, 4 mmol) was added and stirring continued for 3 hr at 0° C. An equal amount of water-treated phosphoryl chloride was again added and the reaction mixture stored for 2 days at 4° C. The reaction mixture was then passed through a column of Dowex 50W-X8 (H+ form, 100–200 mesh, 2.5×13 cm) with water as the eluting solvent. The fractions containing TRMP were combined and the solution lyophilized. The resulting gum was dissolved in 5 ml of water and passed through a column of Bio-Rad AG1-X2 ($CO_3^{-2}$ form, 100–200 mesh, 2.5×12 cm) and eluted first with 500 mL of water followed by 1000 ml of 0.7 M ammonium carbonate. Lyophilization of the first 500 mL of the ammonium carbonate eluent gave 0.97 g (71%) of a white solid which was homogeneous on HPLC. In addition, the material was identical to an authentic sample of TRMP.

EXAMPLE 2

2-(2',3'-Isopropylidene-β-D-ribofuranosyl)-thiazole-4-carboxamide (1c)

To a solution of 1a (1.0 g, 3.8 mmol) and triethylorthoformate (0.6 g, 4 mmol) in acetone (25 ml), 0.5 mL of 1 M HCl in ethyl ether was added and the reaction mixture stirred at room temperature overnight. After neutralizing with conc ammonium hydroxide the reaction mixture was concentrated in vacuo and dissolved in 15 mL of water. The aqueous solution was then extracted with ethyl acetate (7×50 mL) and the resulting organic solution dried ($Na_2SO_4$) and concentrated in vacuo. The recovered oil was purified by preparative HPLC over silica using ethyl acetate as the eluting solvent (Waters LC-500, Prep Pak-500/silica). The fraction corresponding to product was concentrated and recrystallized from ethyl acetate to give 0.83 g (73%) of 1c as white cubes, mp 119°–120°.

EXAMPLE 3

Diammonium salt of
2-(2',3'-Isopropylidene-β-D-ribofuranosyl)-thiazole-4-carboxamide 5'-Phosphate (1d)

Phosphoryl chloride (0.9 g, 2 mmol) was added to a stirred solution of 1c (0.6 g, 2 mmol) in triethyl phosphate (3 mL) at 4° C. The reaction mixture was then stirred for 3 hr and stored in the freezer (−20° C.) for 3 days. After washing the reaction mixture with hexane (3×50 mL), 50 mL of water was added and the pH adjusted to ca 9 using concentrated ammonium hydroxide. The resulting solution was then applied to a column of Bio-Rad AG1-X2 ($CO_3^{-2}$ form, 100–200 mesh, 1.5×80 cm) and eluted with 500 ml of water followed by a 0.5 M ammonium carbonate solution. The first 700 ml of the ammonium carbonate eluent contained 0.32 g of a white solid which was obtained after lyophilization. This material was found to be a mixture of TRMP (RT=9.5 min) and the desired isopropylidene-TRMP (RT=11.5 min) by HPLC. The next 1300 mL contained 0.065 g of the desired compound (RT=11.5 min) which was obtained after lyophilization. This material gave the correct $^1$H-NMR spectrum and was used as such for the synthesis of ITAD. When the initial fraction containing both products was heated (70° C.) with 10% acetic acid (50 mL) for 2 hr, the only compound detected by HPLC was the deprotected TRMP.

EXAMPLE 4

4-Morpholine N,N'-dicyclohexylcarboxamidinium adenosine-5'-phosphoromorpholidate (2b)

This material was prepared in 94% yield as reported previously by Moffat and Khorana, *J. Am. Chem. Soc.*, Vol. 83, pp. 659, 1961. HPLC analysis showed a single peak (RT=7 min). AMP had a retention time of 10 min.

EXAMPLE 5

Adenosine 5'-phosphonic di-n-butylphosphinothioic anhydride (2c)

This material was prepared in 71% yield following the same methodology of Furusawa et al, *J. Chem. Soc. Perkin I*, 1976, 1711.

EXAMPLE 6

2-β-Ribofuranosylthiazole-4-carboxamide 5'→5' adenosine pyrophosphate (3a)

Method a. To a solution of 1b (0.150 g, 0.40 mmol) in pyridine (10 mL), tri-n-octylamine (0.157 g, 0.44 mmol) was added and the resulting solution concentrated in vacuo. The residue was redissolved in pyridine and evaporated in vacuo several times. Separately, a solution of 2b (0.271 g, 0.38 mmol) in pyridine (10 mL) was rendered anhydrous by a similar process of dissolving it in pyridine (10 mL) and evaporating the solution several times. Finally, the two salts were mixed with the aid of 10 mL of pyridine and the new solution was again reduced to dryness and kept under high vacuum for 14 hrs. After redissolving the mixture in 20 mL of dry pyridine and stirring it at 60° C. for 1 hr, HPLC analysis of an aliquot showed only trace amounts of the morpholidate. Heating was continued for one more hour, after which time the reaction mixture was reduced to dryness. Water (30 mL) and sodium acetate (0.1 g) were added to the residue and stirred for a few minutes. The resulting mixture was extracted with ether (2×30 mL) and the first ether extract was reextracted with water (20 mL). All the aqueous extracted were combined and the pH of the solution adjusted to 3 with cation exchange resin (Bio-Rad AG 50W-X8 (H+ form)). The total volume was then reduced to 1 mL and loaded onto a Hamilton HA-X4 ($HCO_2$ form) column. Elution was performed with a linear gradient of water (100 mL) and 2 M ammonium formate (100 mL). Two major fractions containing TAD were collected and each fraction was again rechromatographed on the same column with a linear gradient of water (100 mL) and a mixture of 100 mL of ammonium formate plus formic acid, final molarities 2 M and 2.6 M, respectively. This system provided 20 mg (10%) of pure TAD according to HPLC and NMR analyses. When the above reaction was repeated using half the amount indicated above, and under stirring for 6 days at room temperature, the isolated yield of TAD was 12%.

Method b. TRMP (1b) (0.27 g, 0.72 mmol) was dissolved in formamide (5 mL) and added to a solution of 2c (0.7 g, 1.43 mmol) in pyridine (50 mL). The resulting solution was concentrated in vacuo and dissolved in 6 mL of dry pyridine. Silver nitrate (0.91 g, 5.36 mmol) was added and the mixture stirred for 36 hr. After the addition of water (70 mL), $H_2S$ was bubbled into the reaction mixture and the black precipitate formed removed by filtration. The filtrate was lyophilized and the resulting syrupy liquid was diluted with 5 mL of water and applied to a column of Bio-Rad AG1-X2 ($HCO_2$ form, 100–200 mesh, 1.5×5 cm) and eluted with water (50 ml) followed by 2 M ammonium formate (50 ml). The ammonium formate fraction was lyophilized several times, redissolved in water and precipitated with ethanol. The precipitate that formed was saved and the filtrate concentrated and treated again with ethanol. The combined precipitates (0.325 g) were chromatographed on a Hamilton HA-X4 column as in Method a. to afford 0.08 g of TAD which eluted as a single peak. An extra 5 mg of TAD was obtained from a third precipitation of the mother solution bringing the total yield to 0.085 g (16%).

Analysis: Calculated for $C_{19}H_{29}N_8O_{14}P_2S.2.5H_2O$ (monoammonium salt): C, 31.14; H, 4.51; N, 15.30; P, 8.47; S, 4.37.

Found: C, 31.16; H, 4.63; N, 15.67; P, 8.53; S, 4.14. These results were reproducible and are consistent with the monoammonium salt of TAD. The remaining phosphate anion must accordingly form an inner salt with a basic amino group of either TR or adenosine.

EXAMPLE 7

2-(2,3-Isopropylidine-β-D-ribofuranosyl)-thiazole-4-carboxamide 5→5'-adenosine pyrophosphate (3b)

Compound 1d (0.030 g, 75 mol) was treated with the adenosine phosphoromorpholidate 2b (0.048 g, 65 mol) and tri-n-octylamine (0.0266 g, 25 mol) in an analogous manner as in the synthesis of TAD. After the reaction mixture was kept for 1 hr at 60° C., an aliquot was evaporated, treated with sodium acetate and water, and extracted with ether. The aqueous layer was concentrated in vacuo and examined by HPLC. There were peaks with retention times of 14, 15 and 16 min. After treating part of this aliquot with Bio-RAd AG 50W-X8 (H+ form) and heating for 10 min at 50° C., HPLC analysis revealed that the peak with retention time of 14 min had increased at the expense of the peak with retention time of 16 min. This latter peak, suspected of being the product, was used to monitor the reaction. The reaction mixture was heated for an additional hour and left at room temperature overnight. Following a similar workup as for the aliquot, the aqueous layer afforded a yellowish solid after lyophilization. This material was purified by passing it through a Hamilton HA-X4 (HCO$_2$ form) column to afford ITAD (11.4 mg) as a white solid. Treatment of ITAD (2 mg) with 10% acetic acid for 25 min at 70° C. afforded 1.7 mg of a white fluffy solid after lyophilization. This material was identical to TAD according to the chemical, spectral, and biological criteria.

In this application and claims where the isopropylidene modification is utilized, it was selected predominantly to prove structure.

In this specification and claims where the term pyridine is utilized, it is designed to include methyl ring substituted pyridines such as the picolines, which are methyl substituted, and the lutidines, which are dimethyl substituted.

We claim:
1. 2-β-D-Ribofuranosylthiazole-4-carboxamide 5'→5'-adenosine pyrophosphate and pharmaceutically acceptable acid addition salts.

* * * * *